US005100675A

United States Patent [19]

[11] Patent Number: 5,100,675

[45] Date of Patent: Mar. 31, 1992

Cho et al.

[54] SUSTAINED RELEASE TABLET COMPRISING LORATADINE, IBUPROFEN AND PSEUDOEPHEDRINE

[75] Inventors: Wing-Kee P. Cho, Princeton; Winston A. Vadino, Whitehouse Station; Imtiaz A. Chaudry, Denville, all of N.J.

[73] Assignee: Schering Corporation, Kenilworth, N.J.

[21] Appl. No.: 612,633

[22] Filed: Nov. 13, 1990

Related U.S. Application Data

[62] Division of Ser. No. 346,687, May 3, 1989, Pat. No. 4,990,535.

[51] Int. Cl.[5] .................... A01N 37/30; A01N 37/00; A61K 9/22

[52] U.S. Cl. .................................... 424/468; 514/557; 514/964; 514/290; 514/556

[58] Field of Search ............... 514/556, 290, 964, 557; 424/468

[56] References Cited

U.S. PATENT DOCUMENTS

| | | | |
|---|---|---|---|
| 4,282,233 | 8/1981 | Villane | 514/290 |
| 4,540,566 | 9/1985 | Davis et al. | 424/22 |
| 4,659,716 | 4/1987 | Villani et al. | 514/290 |
| 4,738,966 | 4/1988 | Sunshine et al. | 514/277 |
| 4,780,322 | 10/1988 | Martani et al. | 424/501 |
| 4,783,465 | 11/1988 | Sunshine et al. | 514/255 |
| 4,829,064 | 5/1989 | Sunshine et al. | 514/290 |
| 4,871,733 | 10/1989 | Sunshine | 514/212 |
| 4,999,189 | 3/1991 | Kogan et al. | 424/79 |

*Primary Examiner*—Frederick E. Waddell
*Assistant Examiner*—T. J. Criares
*Attorney, Agent, or Firm*—John J. Maitner; Anita W. Magatti; Eric S. Dicker

[57] ABSTRACT

Pharmaceutical compositions for use in the treatment of cough/cold symptoms comprising loratadine, ibuprofen and pseudoephedrine are disclosed.

10 Claims, No Drawings

SUSTAINED RELEASE TABLET COMPRISING LORATADINE, IBUPROFEN AND PSEUDOEPHEDRINE

This is a division of application Ser. No. 07/346,687, filed May 3, 1989, now U.S. Pat. No. 4,990,535.

BACKGROUND OF THE INVENTION

The present invention relates generally to novel pharmaceutical compositions of matter comprising the non-sedating antihistamine loratadine or the decarbalkoxylation product thereof (i.e. 6-chloro-6, 11- dihydro-11-(4-piperidylidene)-5H-benzo[5,6]cyclohepta [1,2-b]-pyridine), in combination with the non-steroidal anti-inflammatory drug ibuprofen, the decongestant pseudoephedrine, and suitable pharmaceutically acceptable non-toxic carriers or excipients, and to methods of using said compositions in the treatment, management or mitigation of cough, cold, cold-like and/or flu symptoms and the discomfort, pain, fever and general malaise associated therewith.

Non-narcotic analgesics, most of which are also known as non-steroidal anti-inflammatory drugs, such as ibuprofen, are widely administered orally in the treatment of mild to severe pain, and have been disclosed as useful in treating cough/cold symptoms in combination with certain antihistamines and decongestants. See, for example U.S. Pat. Nos. 4,552,899, 4,619,334 and 4,783,465, all to Sunshine et al.

SUMMARY OF THE INVENTION

It is a primary object of the present invention to provide a novel sustained release pharmaceutical composition of matter comprising a combination of an analgesically effective amount of ibuprofen, an antihistaminic-effective amount of loratadine and a decongestant-effective amount of pseudoephedrine in a pharmaceutically acceptable carrier.

It is a further object of the present invention to provide methods for the symptomatic relief of cough, cold, cold-like and flu symptoms by the administration of preselected dosages of the pharmaceutical compositions of the present invention. Cold-like symptoms as used herein refers to coryza, nasal congestion, upper respiratory infections, allergic rhinitis, otitis, sinusitis, etc.

DETAILED DESCRIPTION OF THE INVENTION

A combination dosage form especially suitable for administration of a combination comprising ibuprofen, loratadine or its decarbalkoxylation product, and pseudoephedrine or a pharmaceutically acceptable salt thereof is disclosed. The dosage form provides for the sustained release of ibuprofen and pseudoephedrine or a salt thereof, preferably the sulfate, and the immediate release of loratadine or its decarbalkoxylation product, since the latter are inherently long-acting. Release of ibuprofen and pseudoephedrine takes place over 2 to 16 hours, preferably 5 to 12 hours. One or two, preferably two tablets are administered at a time. Concentration ranges for the actives are as follows: pseudoephedrine salt, 30–240 mg/tablet; ibuprofen, 100–800 mg/tablet; and loratadine or its decarbalkoxylation product, 0.5–10 mg/tablet. The concentration ranges represent about 3 to about 25% of coated tablet weight for pseudoephedrine salt, about 10 to about 55% for ibuprofen, and about 0.05 to about 1.5% for loratadine.

The preferred dosage form is a coated tablet, wherein loratadine or its decarbalkoxylation product is present in the tablet coating and ibuprofen and the pseudoephedrine salt are present in the tablet core, which core also comprises a swellable hydrophilic polymer as a binder. When the dosage form comes into contact with gastric or aqueous media, the coating dissolves rapidly to release loratadine and the core hydrates and slowly releases ibuprofen and pseudoephedrine by erosion of the hydrated layer and/or by diffusion of drug through the core. The rate and duration of release is controlled by the relative concentration of the hydrophilic polymer, as well as by the particular characteristics of the hydrophilic polymer selected.

Loratadine, the USAN chemical name of which is ethyl 4-(8-chloro-5,6-dihydro-11H-benzo[5,6]cyclohepta[1,2-b]pyridin-11-ylidene)-11-piperidinecarboxylate, is claimed in U.S. Pat. No. 4,282,233, and its decarbalkoxylation product, 8-chloro-6,11-dihydro-11-(4-piperidylidene)-5H-benzo [5,6]cyclohepta[l,2-b]pyridine, claimed in U.S. Pat. No. 4,659,716. Pharmaceutically acceptable salts of loratadine and its decarbalkoxylation product are also contemplated for use in the present invention. The dosage range for both loratadine and its decarbalkoxylation product is about 0.5 to about 10 mg per day, preferably about 5 to about 10 mg/day, depending on the age, weight, condition, etc. of the patient.

Typical swellable hydrophilic polymers include cellulosic ethers such as methylcellulose, hydroxypropylcellulose, hydroxymethylcellulose, hydroxyethylcellulose, carboxymethylcellulose and carboxyethylcellulose, or mixtures thereof, with hydroxypropylmethylcellulose (HPMC) being preferred. Particularly useful HPMC polymers are HPMC USP 2910 and USP 2208, for example The Dow Chemical Company's METHOCEL E4M, E15M and K100M, wherein tee designation "E" refers to USP 2910 and the designation "K" refers to USP 2208, and wherein the number designation refers to the viscosity in a 2% aqueous solution (e.g. 4M designates a viscosity of 4000 cps) and indicates the number average molecular weight (Mn) of the polymers (E4M has Mn 86,000, E15M has Mn 120,000, and K100M has Mn 246,000). The hydrophilic polymer or polymer mixture is present at a concentration of about 5 to about 15% of the tablet core weight.

The tablet core optionally further comprises excipients such as insoluble polymers, soluble or insoluble fillers, antiadherents, lubricants and additional binders. Typical fillers include dibasic calcium phosphate and the dihydrate thereof, microcrystalline cellulose and lactose, with microcrystalline cellulose being preferred. Fillers are present at a concentration of about 10% to about 20% of the tablet core weight. Antiadherents, used to prevent tablets from sticking to the tablet press, typically include silicas such as silicon dioxide and talc, and are present at a concentration of 0 to about 5% of the tablet core weight. Typical lubricants are magnesium stearate and stearic acid, present at a concentration of about 0.25 to about 5% of the tablet core weight. Additional binders used in the granulation of the drug-polymer mixture typically include povidone and cornstarch. Such binders are present at a concentration of about 0.5 to about 3% of the tablet core weight.

The tablet coating comprises, in addition to the active, a hydrophilic polymer as described above, preferably HPMC, and a plasticizer such as polyethylene glycol (PEG). A preferred HPMC for tablet coating is HPMC 2910 having a viscosity of 4–60 cps in a 2% aqueous solution, more preferably having a viscosity of 6 cps. The PEG preferably has a molecular weight of 300–6000. The ration of polymer to plasticizer is about 2:1 to about 5:1, with 5:1 being preferred.

For preferred compositions of the present invention, either the ibuprofen or the pseudoephedrine (or salt thereof) is also coated with HPMC-PEG as described for the tablet coating in order to avoid stability problems arising from the physical incompatibility of ibuprofen and pseudoephedrine.

The methods of preparing compositions of the present invention, e.g. granulation, table compression and table coating, are all well known to those skilled in the art.

EXAMPLE 1

| | mg/tablet |
|---|---|
| A. Core Tablet | |
| Pseudoephedrine Sulfate | 120 |
| Ibuprofen 90%* | 555 |
| HPMC K100M | 100 |
| Povidone | 10 |
| Microcrystalline Cellulose | 154 |
| HPMC/PEG | 28 |
| Magnesium Stearate | 5 |
| | 972 |
| B. Active Coating | |
| Loratadine | 5 |
| HPMC/PEG | 10 |

*Equivalent to 500 mg ibuprofen

Method of Manufacture

A. Core

1. Blend pseudoephedrine sulfate, microcrystalline cellulose and HPMC K100M for 5–30 minutes in a suitable mixer.

2. Dissolve povidone in a hydroalcoholic mixture and use it to granulate the powder mix.

3. Dry and mill the pseudoephedrine sulfate granulation using suitable size screen.

4. Coat ibuprofen with HPMC/PEG solution in a suitable coater (see part B below).

5. Blend the screened pseudoephedrine sulfate granulation with coated ibuprofen and remaining ingredients for 3–15 minutes.

6. Compress into suitable size tablets.

B. Ibuprofen coating

1. Dissolve HPMC and PEG in suitable amount of water.

2. Coat ibuprofen with the HPMC/PEG solution in a suitable coater.

C. Active Loratadine Coating

1. Dissolve HPMC/PEG in suitable amount of water or a water/alcohol mixture.

2. Disperse loratadine in the HPMC/PEG solution.

3. Coat tablets with the dispersion and polish the coated tablets using standard procedures.

EXAMPLE 2

| | mg/tablet |
|---|---|
| A. Core | |
| Pseudoephedrine Sulfate | 120 |
| Ibuprofen 90%* | 555 |
| HPMC E4M | 150 |
| Povidone | 7.5 |
| Microcrystalline Cellulose | 148.5 |
| Silicon Dioxide | 14 |
| Magnesium Stearate | 5 |
| | 1000 |
| B. Coating | |
| Loratadine | 5 |
| HPMC/PEG | 10 |

*Equivalent to 500 mg ibuprofen

Method of Manufacture

A. Core

1. Blend pseudoephedrine sulfate, microcrystalline cellulose and HPMC E4M for 5–30 minutes in a suitable mixer.

2. Dissolve povidone in a hydroalcoholic mixture and use it to granulate the powder blend.

3. Dry and mill the pseudoephedrine sulfate granulation using suitable size screen.

4. Blend the pseudoephedrine sulfate granulation, ibuprofen and remaining ingredients for 3–15 minutes.

5. Compress into suitable size tablets.

B. Active Loratadine Coating

1 Dissolve HPMC and PEG in suitable amount of water.

2. Disperse loratadine in the HPMC/PEG solution.

3. Coat tablets with the dispersion and polish the coated tablets using standard procedures.

A similar dosage form comprising the non-steroidal anti-inflammatory drug acetaminophen in place of ibuprofen is also a part of the present invention. The dosage form releases acetaminophen and pseudoephedrine over 2 to 16 hours, preferably 5 to 12 hours, and immediately releases loratadine. Concentration ranges for the actives are as follows: pseudoephedrine salt, 30–240 mg/tablet; acetaminophen, 100–500 mg/tablet; and loratadine or its decarbalkoxylation product, 0.5–10 mg/tablet. The concentration ranges represent about 3 to about 35% of coated tablet weight for pseudoephedrine salt, about 10 to about 65% for acetaminophen and about 0.05 to about 1.5% for loratadine.

The hydrophilic polymers are present at a concentration of about 5 to about 15%, fillers at about 10 to about 20%, antiadherents at 0 to about 5%, lubricants at 0.25 to about 5%, and binders at 0 to about 3%, all percentages being relative to the tablet core weight.

The tablet coating comprises the loratadine or its decarbalkoxylation product, a hydrophilic polymer and a plasticizer as described above, i.e. a preferred polymer is HPMC USP 2910 and a preferred plasticizer is PEG, present in a preferred ratio of 5:1.

The following example is directed to a loratadine, acetaminophen and pseudoephedrine sulfate combination dosage form.

EXAMPLE 3

| | mg/tablet |
|---|---|
| A. Core Tablet | |
| Pseudoephedrine Sulfate | 60 |
| Acetaminophen 90%* | 555 |
| Dicalcium phosphate dihydrate | 98 |

-continued

| | mg/tablet |
|---|---|
| HPMC E4M | 48 |
| Stearic Acid | 10 |
| Magnesium Stearate | 4 |
| | 775 |
| B. Active Coating | |
| Loratadine | 2.5 |
| HPMC/PEG | 5.0 |

*Equivalent to 500 mg acetaminophen

Method of Manufacture

A. Core

1. Blend pseudoephedrine sulfate, acetaminophen, dicalcium phosphate dihydrate and HPMC E4M for 5-30 minutes in a suitable mixer.

2. Granulate the powder mix with a hydroalcoholic mixture.

3. Dry and mill the granulation using suitable size screen.

4. Compress into suitable size tablets.

B. Active Loratadine Coating

1. Dissolve HPMC/PEG in suitable amount of water or a water/alcohol mixture.

2. Disperse loratadine in the HPMC/PEG solution.

3. Coat tablets with the dispersion and polish the coated tablets using standard procedures.

While the invention has been described and illustrated with reference to certain preferred embodiments thereof, those skilled in the art will appreciate that various changes, modifications and substitutions can be made therein without departing from the spirit of the invention. For example, effective dosages of the active ingredients other than the preferred ranges set forth hereinabove may be used based on such factors as the age, weight and condition of the patient. It is intended that the invention be limited only by the scope of the claims which follow.

We claim:

1. A sustained release pharmaceutical composition comprising a coated tablet wherein the tablet coating comprises an antihistaminic-effective amount of loratadine or 6-chloro-6,11-dihydro-11-(4-piperidylidene)-5-H-benzo [5,6]cyclohepta[1,2-b]pyridine and a hydrophilic polymer and the tablet core comprises an analgesic-effective amount of acetaminophen, a decongestant-effective amount of pseudoephedrine or a pharmaceutically acceptable salt thereof and a swellable hydrophilic polymer, and wherein the tablet coating and the tablet core further comprise pharmaceutically acceptable excipients.

2. A composition of claim 1 wherein the tablet core comprises acetaminophen at about 10 to about 65% of the coated tablet weight, pseudoephedrine or a pharmaceutically acceptable salt thereof at about 3 to about 35% of the coated tablet weight, and a hydrophilic polymer at about 5 to about 15% of the tablet core weight.

3. A composition of claim 2 wherein the tablet core further comprises about 10 to about 20% filler, 0 to about 5% antiadherent, about 0.25 to about 5% lubricant and 0 to about 3% binder.

4. A composition of claim 2 wherein the hydrophilic polymer is a cellulosic ether selected from the group consisting of methylcellulose, hydroxypropylcellulose, hydroxymethylcellulose, hydroxyethylcellulose, carboxymethylcellulose, carboxyethylcellulose and mixtures thereof.

5. A composition of claim 3 wherein the filler is dibasic calcium phosphate or the dihydrate thereof, microcrystalline cellulose or lactose and the lubricant is magnesium stearate or stearic acid.

6. A composition of claim 3 wherein the hydrophilic polymer is hydroxypropylmethylcellulose USP 2910 or is hydroxypropylmethylcellulose USP 2208 having a viscosity of 100,000 cps in a 2% aqueous solution; the filler is dibasic calcium phosphate dihydrate; and the lubricant is magnesium stearate and stearic acid.

7. A composition of claim 1 wherein the tablet coating comprises loratadine or 6-chloro-6,11-dihydro-11-(4-piperidylidene)-5H-benzo [5,6]cyclohepta[1,2-b]pyridine at a concentration of about 005to about 1.5% of the coated tablet weight, and wherein the tablet coating further comprises hydroxypropylmethylcellulose and polyethylene glycol in a ratio of about 2:1 to about 5:1.

8. A composition of claim 7 wherein the hydroxypropylmethylcellulose is hydropropylmethylcellulose USP 2910 having a viscosity of 4–60 cps in a 2% aqueous solution, and the polyethylene glycol has a molecular weight of 300-6000.

9. A composition of claim 1 wherein the tablet core comprises 60 mg pseudoephedrine sulfate, 555 mg acetaminophen 90%, 48 mg hydroxypropylmethylcellulose USP 2910 having a viscosity of 4000 cps in a 2% aqueous solution, 98 dibasic calcium phosphate dihydrate, 10 mg stearic acid and 4 mg magnesium stearate, and wherein the tablet coating comprises 2.5 mg loratadine and 5 mg of a 5:1 mixture of hydroxypropylmethylcellulose USP 2910 having a viscosity of 6 cps in a 2% aqueous solution and polyethylene glycol having a molecular weight of 300–6000.

10. A method of treating cold, cold-like and flu symptoms comprising administering a composition of claim 1 to a mammal in need of such treatment.

* * * * *